United States Patent
Ramuz et al.

(10) Patent No.: US 8,503,073 B2
(45) Date of Patent: Aug. 6, 2013

(54) LIGHT COUPLING DEVICE AND SYSTEM, AND METHOD FOR MANUFACTURING THE DEVICE AND SYSTEM

(75) Inventors: Marc Ramuz, St-Louis (FR); David Leuenberger, Basel (CH); Carsten Jochen Winnewisser, Freiburg im Breisgau (DE); Ross Stanley, Epalinges (CH); Lukas Bürgi, Zürich (CH)

(73) Assignee: CSEM Centre Suisse d'Electronique et de Microtechnique S.A.—Recherche et Developpement, Neuchatel (CH)

( * ) Notice: Subject to any disclaimer, the term of this patent is extended or adjusted under 35 U.S.C. 154(b) by 897 days.

(21) Appl. No.: 12/487,980

(22) Filed: Jun. 19, 2009

(65) Prior Publication Data

US 2009/0316429 A1 Dec. 24, 2009

Related U.S. Application Data

(60) Provisional application No. 61/075,282, filed on Jun. 24, 2008.

(51) Int. Cl.
*H01S 5/10* (2006.01)
*H01S 5/04* (2006.01)

(52) U.S. Cl.
CPC ........... *H01S 5/1035* (2013.01); *H01S 5/041* (2013.01); *H01S 5/1039* (2013.01); *Y10S 977/95* (2013.01)
USPC .......................................... 359/344; 977/950

(58) Field of Classification Search
CPC ................................ H01S 5/1035; H01S 5/041
USPC ...................................... 359/344; 372/46.015
See application file for complete search history.

(56) References Cited

U.S. PATENT DOCUMENTS

| 3,901,738 A * | 8/1975 | Hunsperger et al. ...... 372/46.015 |
| 4,904,045 A * | 2/1990 | Alferness et al. ............... 385/37 |
| 5,045,498 A * | 9/1991 | Wang et al. ...................... 438/45 |
| 5,140,149 A * | 8/1992 | Sakata et al. ................... 257/436 |
| 5,444,730 A * | 8/1995 | Mizutani ..................... 372/45.01 |
| 5,485,021 A * | 1/1996 | Abe ................................. 257/84 |

(Continued)

FOREIGN PATENT DOCUMENTS

WO 03094256 A2 11/2003

OTHER PUBLICATIONS

Ficke, L.; Cahay, M.; , "The bright future of organic LEDs," Potentials, IEEE , vol. 22, No. 5, pp. 31-34, Dec. 2003-Jan. 2004 doi: 10.1109/MP.2004.1301245 URL: http://ieeexplore.ieee.org/stamp/stamp.jsp?tp=&arnumber=1301245&isnumber=28912.*

(Continued)

*Primary Examiner* — Mark Hellner
*Assistant Examiner* — Ari M Diacou
(74) *Attorney, Agent, or Firm* — A.C. Entis-IP Ltd.

(57) ABSTRACT

Embodiments of the disclosed technique disclose an optical device generating light by luminescence comprising a substrate, a waveguide, a pump light source and a photoluminescent layer, wherein the waveguide is positioned between the substrate and the photoluminescent layer, or the photoluminescent layer is positioned between the substrate and the waveguide. The pump light source is provided opposite to the photoluminescent layer at the backside of the substrate. The pump light source is adapted to pump the photoluminescent layer to emit light; and at least some of the emitted light is evanescently coupled into the waveguide.

20 Claims, 9 Drawing Sheets

U.S. PATENT DOCUMENTS

| | | | | |
|---|---|---|---|---|
| 5,613,020 | A | * | 3/1997 | Uchida et al. .................... 385/9 |
| 5,648,978 | A | * | 7/1997 | Sakata ...................... 372/50.11 |
| 5,719,892 | A | * | 2/1998 | Jiang et al. ................ 372/50.11 |
| 5,874,803 | A | * | 2/1999 | Garbuzov et al. ............ 313/506 |
| 5,907,160 | A | | 5/1999 | Wilson et al. |
| 5,949,187 | A | * | 9/1999 | Xu et al. ...................... 313/504 |
| 6,160,273 | A | * | 12/2000 | Fork et al. ...................... 257/98 |
| 6,215,585 | B1 | * | 4/2001 | Yoshimura et al. .......... 359/344 |
| 6,472,817 | B1 | * | 10/2002 | Kawase ........................ 313/504 |
| 6,538,808 | B1 | * | 3/2003 | Tastavridis .................. 359/344 |
| 6,693,937 | B2 | * | 2/2004 | Steffens ...................... 372/50.1 |
| 6,704,335 | B1 | | 3/2004 | Koyama et al. |
| 6,795,472 | B2 | * | 9/2004 | Akulova et al. .............. 372/50.1 |
| 6,813,431 | B2 | * | 11/2004 | Davids et al. ................ 385/129 |
| 7,126,750 | B2 | * | 10/2006 | Wasserbauer ................ 359/344 |
| 7,711,221 | B2 | * | 5/2010 | Burgi et al. .................... 385/30 |
| 2001/0026857 | A1 | * | 10/2001 | Kinoshita .................... 428/105 |
| 2002/0085270 | A1 | * | 7/2002 | Bendett ........................ 359/343 |
| 2003/0156617 | A1 | * | 8/2003 | Baney et al. .................... 372/96 |
| 2003/0203210 | A1 | | 10/2003 | Graff et al. |
| 2003/0219058 | A1 | * | 11/2003 | Kahen et al. .................... 372/96 |
| 2004/0109485 | A1 | * | 6/2004 | Flory et al. ...................... 372/45 |
| 2004/0264528 | A1 | * | 12/2004 | Kruschwitz et al. ............ 372/39 |
| 2005/0201899 | A1 | * | 9/2005 | Weisbuch .................. 422/82.11 |
| 2005/0249509 | A1 | * | 11/2005 | Nagarajan et al. ............ 398/198 |
| 2006/0050364 | A1 | * | 3/2006 | Ratowsky et al. ............ 359/333 |
| 2006/0186801 | A1 | * | 8/2006 | West .............................. 313/506 |
| 2007/0019899 | A1 | * | 1/2007 | Ohtsu et al. .................... 385/14 |

OTHER PUBLICATIONS

Nakahama, M., Shimada, T., & Koyama, F. (2012). Lateral integration of MEMS VCSEL and slow light amplifier boosting single mode power. IEICE Electronics Express, 9(6), 544-551. Retrieved from http://joi.jlc.jst.go.jp/JST.JSTAGE/elex/9.544?from=CrossRef.*

European Search Report completed Jan. 10, 2012 for EP Patent Application No. 09163266 filed Dec. 30, 2009 (related application).

Y. Ohmori et al., "Realization of Polymeric Optical Integrated Devices Utilizing Organic Light-Emitting . . . ", IEEE Journal of Selected Topics in Quantum Electronics 10,p. 70 2004.

Y.Y.Lin "100 micron waveguide. 50 micron diffuser particles embedded in waveguide to enhance coupling efficiency" Applied Physics Letters 89, 063501 2006.

Lange, J. et al.; "Recent Innovations in Barrier Technologies for Plastic Packaging—a Review"; Packaging Technology and Science 2003; 16: pp. 149-158.

de Gans, Berend-Jan et al.; "Inkjet Printing of Polymers: State of the Art and Future Developments"; 2004; 16, No. 3; pp. 203-213.

Ramuz, Marc et al.; "High Sensitivity Organic Photodiodes with low dark currents and increased lifetimes"; Elsevier; Organic Electronics 9; 2008; pp. 369-376.

* cited by examiner

US 8,503,073 B2

LIGHT COUPLING DEVICE AND SYSTEM, AND METHOD FOR MANUFACTURING THE DEVICE AND SYSTEM

The present invention claims priority from U.S. provisional patent application 61/075,282 filed on Jun. 24, 2008, the application which is incorporated herein by reference in its entirety.

FIELD OF THE INVENTION

The present invention generally relates to an optical device, system and method according to the preambles of the independent claims that are proposed.

BACKGROUND OF THE INVENTION

Using organic light emitting diodes (OLEDs) as monolithically integrated luminescent source in integrated optical devices might be beneficial in many applications for the following reasons: first, OLEDs can be fabricated by purely additive low-temperature processes such as ink-jet printing and can thus be easily integrated onto almost any substrate. Second, they are ultra-thin and thus offer the potential for being substantially space-saving. Third, via chemical modification of the OLED's light emitting molecule(s) the emission spectrum can be tuned over a wide range of the optical spectrum. Fourth, they are compatible with flexible polymeric substrates. Finally, due to their simple device architecture and processing scheme they hold the promise for low-cost fabrication and integration.

A major challenge pertaining to OLEDs is the coupling of the light emitted there into a low-order mode (less than 20 modes) supporting waveguide. Various publications teach how light emitted from an OLED may be coupled into a waveguide. However, implementations of these publications are not suitable for the coupling of light into a waveguide in low-order modes.

U.S. Pat. No. 5,907,160 discloses a thin film organic light emitting diode with edge emitter waveguide comprising, in sequence, a substrate, a waveguide, an anode, a hole transport layer, an electroluminescent layer, and a cathode. Voltage applied between the anode and cathode causes the electroluminescent layer to emit light through the hole transport layer and the anode into the waveguide where the light is internally reflected within the waveguide and propagates through the length of the waveguide to be emitted through the edge of the waveguide.

U.S. Pat. No. 6,472,817 discloses an organic light emitting device having a first electrode and a transparent electrode with an organic light emitting layer there between; characterized by a waveguide provided on the opposite side of the transparent electrode compared to the organic light emitting layer. In addition, U.S. Pat. No. 6,472,817 also discloses a device incorporating at least two such organic light emitting devices so as to provide a pulsed modulation output or a multi-color output.

U.S. Pat. No. 6,704,335 discloses an edge-emitting type light-emitting device that comprises an organic light-emitting layer, a pair of electrode layers for applying an electric field to the organic light-emitting layer, and an optical waveguide which transmits light emitted from the organic light-emitting layer to the edge. The optical waveguide disclosed in U.S. Pat. No. 6,704,335 further comprises a core layer mainly transmitting light, and cladding layers having a refractive index lower than that of the core layer. The core layer is a layer different from the organic light-emitting layer or comprises the organic light-emitting layer. A grating is formed in the core layer or in the boundary area between the core layer and the cladding layer. A light-emitting device comprises an optical fiber section. Another embodiment comprises a defect and a grating having a one-dimensional periodic refractive index distribution and constituting a photonic band gap. However, implementations of teachings disclosed in U.S. Pat. Nos. 5,907,160, 6,472,817 and 6,704,335 may induce waveguide losses caused by the presence of the OLED itself. Accordingly, implementations of the above-mentioned US patents fail to efficiently couple light emitted from the OLEDs into a low-order mode waveguide.

Further, Y. Ohmori et al. disclose in the publication "Realization of Polymeric Optical Integrated Devices Utilizing Organic Light-Emitting Diodes and Photodetectors Fabricated on a Polymeric Waveguide, IEEE Journal of Selected Topics in Quantum Electronics 10, p. 70, 2004" a 45° cut mirror at one end of a waveguide of 70 µm core size to reflect the light from the OLED on top of the waveguide into the core. However, since the optical power that can be coupled scales with the core size of the waveguide, the approach disclosed by Y. Ohmori et al. may yield insufficient power in the case of low-order mode waveguides.

Y.-Y. Lin et al. disclose in their publication "100 µm waveguide. 50 µm diffuser particles embedded in waveguide to enhance coupling efficiency, Applied Physics Letters 89, 063501, 2006" the introduction of a diffuser layer into the waveguide to couple light from an OLED into a coplanar waveguide. However, diffuser particles may be difficult to integrate into low-order mode waveguides of thicknesses equal to the wavelength of the light they guide. Furthermore, multiple scattering events may constitute a major problem in the case of low-order mode waveguides and limit the achievable coupling efficiency considerably.

U.S. Pat. No. 6,160,273A discloses an OLED-based edge emitter that mitigates the problem of unacceptably large losses by physically separating the OLED from the waveguide using an optical cladding layer. In their preferred embodiment the thickness of the cladding layer between the fluorescent medium/waveguide and the OLED is comparable to the wavelength of the photons generated in the fluorescent medium/waveguide. In their preferred embodiment the fluorescent medium also acts as a waveguide. In case the fluorescent medium cannot provide the required optical confinement, separate sub-structures of fluorescing material and light guiding material are proposed.

BRIEF DESCRIPTION OF THE DRAWINGS

The subject matter regarded as the invention will become more clearly understood in light of the ensuing description of embodiments herein, given by way of example and for purposes of illustrative discussion of the present invention only, with reference to the accompanying Figures, wherein.

DESCRIPTION OF THE EMBODIMENTS OF THE INVENTION

Figure 1A:
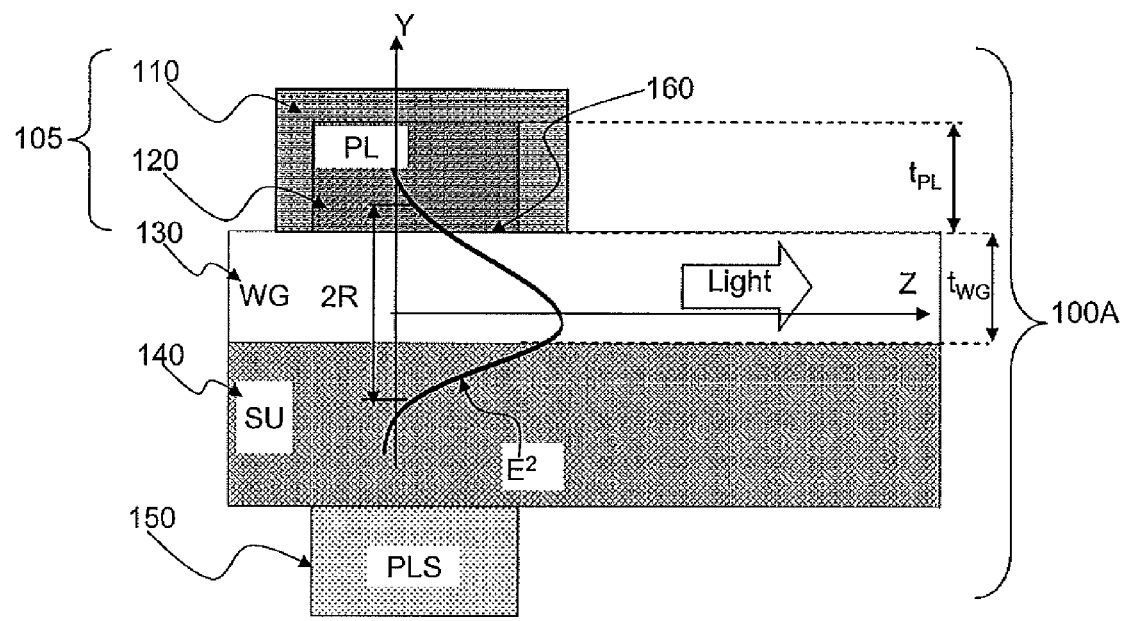
FIG. 1A is a schematic block diagram illustration of a side view of an optical device adapted to pump a photo-luminescent layer with a luminescent light source from the opposite side of the substrate and couple light emitted from the photo-luminescent layer into a low-order mode waveguide, according to an embodiment of the invention.

Summary of the Embodiments of the Disclosed Technique

Embodiments of the disclosed invention provide an optical device generating light by luminescence comprising a substrate, a waveguide, a pump light source and a light source.

In embodiments, the waveguide is mechanically evanescently coupled with a photoluminescent layer of the light source.

In embodiments, the pump light source is provided opposite to the photoluminescent layer at the backside of the substrate.

In embodiments, the pump light source is adapted to pump theotoluminescent layer to emit light; and at least some of said emitted light is evanescently coupled into the waveguide.

In embodiments, the waveguide is positioned between the substrate and the photoluminescent layer.

In embodiments, the photoluminescent layer is positioned between the substrate and the waveguide.

In embodiments, the waveguide is a low-order waveguide with a thickness in the range of 10 nm to 10 μm.

In embodiments, the absorption and emission peak of light emitted by the photoluminescent layer are spectrally separated by at least 50 nm.

In embodiments, the optical device by comprises an encapsulation layer sealing at least the photoluminescent layer of the light source.

In embodiments, the light source comprises a spacer layer and a mirror, wherein the spacer layer has a separation distance $t_{SL}$ and is disposed between the photoluminescent layer and the mirror, the mirror reflecting and re-injecting at least some of the light pumped by the pump light source back into the photoluminescent layer.

In embodiments, the separation distance $t_{SL}$ may be at least twice as large as the penetration depth $L_P$ of a wavefront field into the photoluminescent layer and preferably has a thickness of at least 1 μm.

In embodiments, the optical device comprises an optical filter structure adapted to modify at least some of the light being coupled into the waveguide.

In embodiments the optical filter structured is positioned between the waveguide and the photoluminescent layer.

In embodiments, the optical filter structure is positioned between the substrate and the waveguide.

The present invention further discloses an optical system comprising at least one substrate, at least one waveguide, at least one pump light source, at least one light source, and at least one waveguide.

In embodiments, the at least one waveguide is evanescently coupled with a photoluminescent layer of the at least one light source.

In embodiments, the at least one pump light source is provided on the backside of the substrate opposite to the at least one light source, respectively.

In embodiments, the at least one pump light source is adapted to pump the photoluminescent layer to emit light, and at least some of the emitted light is optically coupled into the at least one waveguide, respectively.

Detailed Description of the Embodiments of Disclosed Invention

The present invention discloses an optical device configured in a manner that enables to couple light emitted from a luminescent source such as, for example but not limited to an organic light emitting diode (OLED), into a low-order mode waveguide. Correspondingly, the present invention enables the usage of luminescent sources in association with waveguides that support only low-order modes. The term "low-order mode" as used herein may refer, in some embodiments of the invention, to less than 20 modes. In some embodiments of the invention, the term "low-order mode" may refer to less than 5 modes. Correspondingly, a low-order waveguide may refer to a waveguide that supports the propagation of light therein at less than 20 modes, and in some embodiments of the invention, at less than 5 modes.

The terms "right", "left", "bottom", "underneath", "below", "lowered", "low", "top", "above", "elevated" and "high" as well as grammatical variations thereof as optionally used herein do not necessarily indicate that, for example, a "bottom" component is below a "top" component, or that a component that is "below" is indeed "below" another component or that a component that is "above" is indeed "above" another component as such directions, components or both may be flipped, rotated, moved in space, placed or provided in a diagonal orientation or position, placed or provided horizontally or vertically, or be similarly modified. Accordingly, it will be appreciated that terms such as "bottom", "below", "underneath" "top" and "above" may be used herein for exemplary purposes only, to illustrate the relative positioning or placement of certain components, to indicate a first and a second component or to do both.

Reference is now made to FIG. 1A. The present invention discloses an optical device generating light by luminescence. In embodiments of the disclosed invention, an optical device 100A includes, inter alia, a low-order mode waveguide (WG) 130 that is mechanically and evanescently coupled with a photoluminescent layer (PL) 120, as well as a luminescent pump light source (PLS) 150 provided at least approximately in alignment with or opposite to PL 120 on the backside of SU 140. Accordingly, SU 140 may be provided between WG 130 and PLS 150. PLS 150 is adapted to optically pump PL 120, e.g., indirectly. In some embodiments, WG 130 is provided on and positioned between a substrate (SU) 140 and a photoluminescent layer (PL) 120. In another embodiment (not shown), the low-order mode waveguide (WG) 130 is provided on one side of the substrate (SU) 140 and the luminescent pump light source (PLS) 150 is still provided on the backside of SU 140 but the photoluminescent layer (PL) 120 is placed or provided between the waveguide 130 and the substrate SU 140.

In some embodiments, PL 120 is mechanically coupled with WG 130 in a manner such that at least some of the light re-emitted by PL 120 is coupled, e.g., as known in the art, evanescently to the low-order modes of into WG 130.

It should be noted that the term "evanescently coupling" as well as grammatical variations thereof may refer to the case wherein the vertical distance along Y between any two points of PL 120 and WG 130 may be less than one wavelength of the emitted light.

PL 120 is configured such that its absorption and emission bands are well separated, thus minimizing or at least reducing the re-absorption of light coupled into WG 130. As a matter of fact the power coupled into WG 130 scales at least approximately linearly with the area of PL 120 pumped by PLS 150. It should be noted that in some embodiments (not shown), PL 120 may be located between WG 130 and SU 140.

PLS 150 may be embodied, for example, by a photoluminescent, an electroluminescent, a chemiluminescence or any other suitable additional or alternative material; by inorganic light-emitting diodes (LEDs), laser diodes, an OLED, or any other light emitting material, e.g., as known in the art.

PL 120 may have a thickness ranging from 1 μm to 10 μm. In some preferred embodiment of the invention, thickness of PL 120 may range, for example, from 100 nm to 1 μm.

WG 130 may have a thickness $t_{WG}$ supporting propagation of light in low-order modes only. For example, WG 130 may have a thickness $t_{WG}$ ranging from 10 nm to 10 μm; from 50 nm to 1 μm, or for example, from 100 nm to 500 nm. In preferred embodiments, the thickness of WG 130 is in the range of 100 nm to 300 nm.

Overall thickness $t_{LS}$ of PLS 150 may be at least approximately equal or be smaller than, e.g., 100 μm. In some embodiments of the invention, the thickness $t_{LS}$ of PLS may be at least approximately equal or be smaller than 10 μm, or at least approximately equal or smaller than, for example, 1 μm.

In some embodiments of the invention, optical device 100A may include an encapsulation layer 110 sealing at least PL 120 of light source 105 to protect the latter against potentially damaging environmental influences such as the penetration of oxygen and/or moisture. It should be noted that the term "sealing" as well as grammatical variations thereof also encompass the meaning of the term "substantially sealing" with the respective grammatical variations. By providing encapsulation layer 110, PL 120 is less susceptible to, e.g., photooxidation, and other processes that may modify the optical properties PL 120 and have the potential to degrade the operability of optical device 100A. Moreover, the overall lifetime of the photoluminescent material of PL 120 is increased compared to the lifetime if no encapsulation layer 110 would have been employed.

Figure 1B:
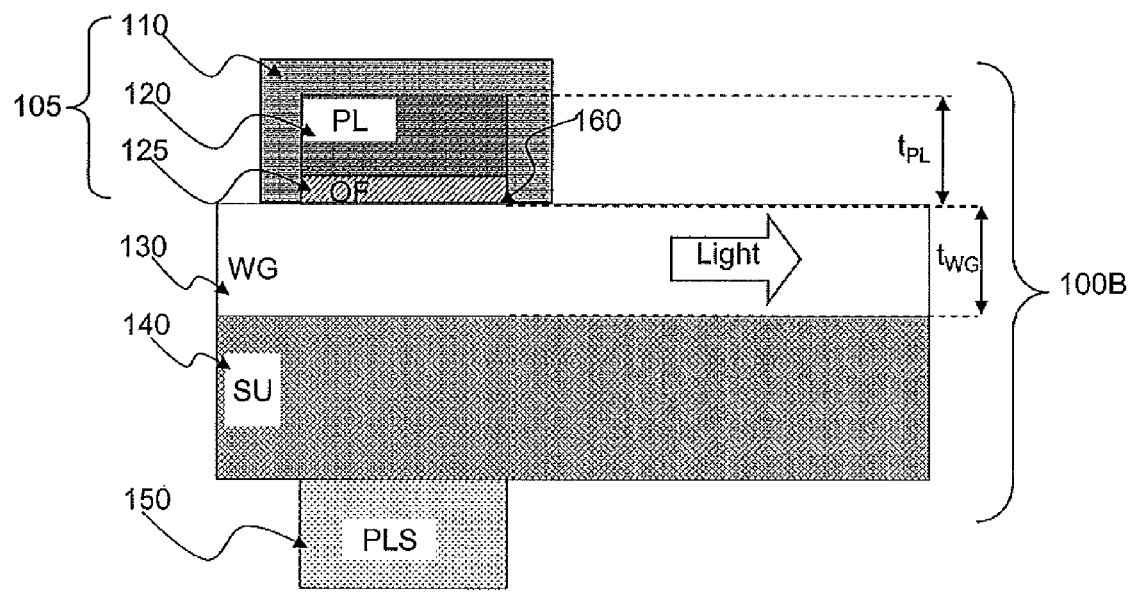
FIG. 1B is a schematic block diagram illustration of a side view of an optical device adapted to couple light emitted from a luminescent source into a low-order mode waveguide, according to an alternative embodiment of the invention.

Additional reference is now made specifically to FIG. 1B. According to some embodiments of the invention, WG 130 of an optical device 100B may include an optical filter structure (OF) 125, which may be positioned between WG 130 and PL 120 and/or between SU 140 and WG 130. OF 125 and PL 120 may constitute light source 105. OF 125 is adapted to modify at least some of the light prior and/or while being coupled into WG 130. Such modification of light, which may occur at an interface 160 between WG 130 and OF 125 may comprise, for example, narrowing the spectra and/or modifying the polarization of light. Such modifications may, for example, cause an increase of the coupling efficiency between PL 120 and WG 130. OF 125 may be embodied, for example, by diffractive gratings, dielectric color filters, polarizers, dichroic filters, liquid crystal devices, or by any combination of the above.

In embodiments of the disclosed technique, PL 120 and WG 130 may be monolithically integrated, i.e., integrally formed with each other. For example, WG 130 may be embodied by a polymer matrix, a photoresist layer or a spin-on-glass doped with a photoluminescent material embodying PL 120. Fabrication processes may include but are not limited to at least one of the following: spin-coating, dip-coating and solgel.

In some embodiments, WG 130 may embody SU 140. The coupling of light with SU 140 may be accomplished, e.g., as known in the art.

PLS 150 may include optically dissipative and/or metallic layers and may thus cause modal loss in WG 130. A metallic layer may, for example, give rise to modal loss of light propagating in WG 130 due to a) surface plasmons and/or b) absorption losses and/or c) quenching, which is hereinafter referred to as non-radiative damping. To at least reduce the modal loss inside WG 130, the latter may be separated from PLS 150 by a given distance corresponding, e.g., to the thickness of SU 140, as is for example schematically illustrated in FIG. 1A. An optical device according to embodiments of the invention may be configured such that modal loss of light propagating in WG 130 is lower than, e.g., 100 cm$^{-1}$. In some preferred embodiments of the invention, modal loss is less than, e.g., 10 cm$^{-1}$. In embodiments, encapsulation layer 110 may seal PL 120 and OF 125.

Figure 2A:
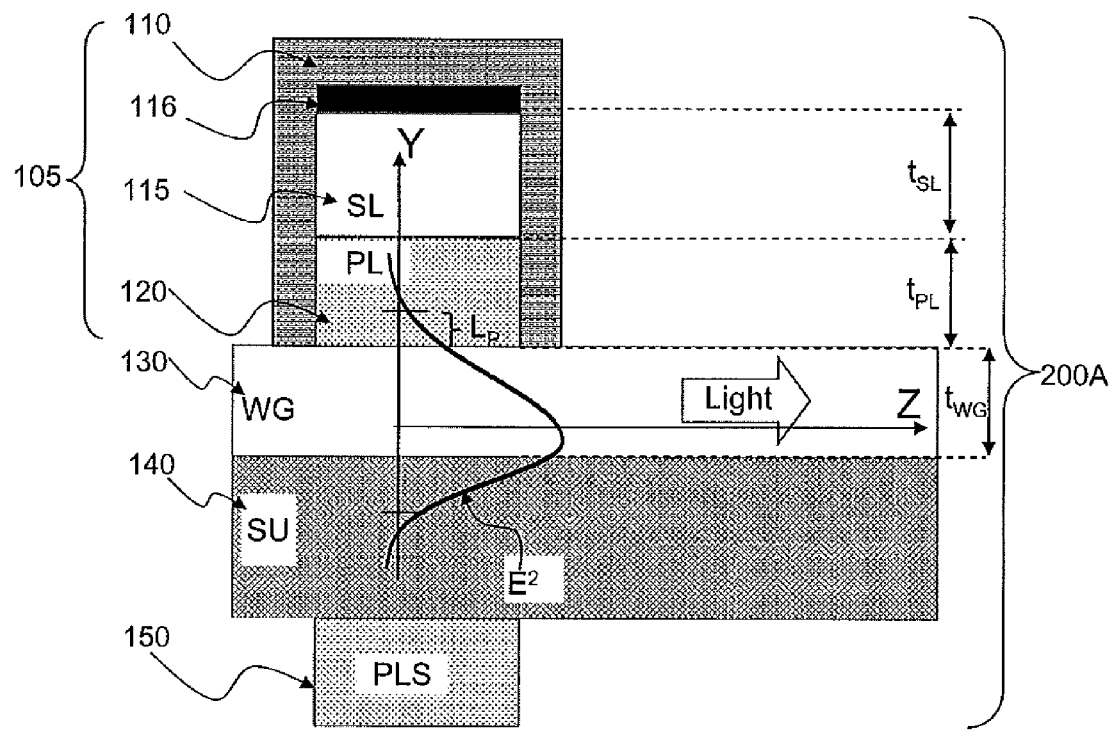
FIG. 2A is a schematic block diagram illustration of a side view of an optical device adapted to couple light emitted from a luminescent source into a low-order mode waveguide with high coupling efficiency based on a far mirror approach, according to a yet alternative embodiment of the invention.

Reference is now made to FIG. 2A. In order to increase the light-coupling from PL 120 into WG 130, light source 105 of an optical device 200A may include a reflective mirror 116 that is placed or provided at some separation distance $t_{SL}$ from PL 120, wherein the separation distance corresponds to the thickness $t_{SL}$ of a spacer layer (SL) 115 that may be disposed between PL 120 and mirror 116 of light source 105. Mirror 116 reflects at least some of the light pumped from PLS 150 that has not been absorbed by PL 120 and re-injects it into PL 120. Ideally, employing mirror 116 increases the amount of light coupled into WG 130 by a factor of 2. The separation distance $t_{SL}$ may be at least twice as large as the penetration depth $L_P$ of a wavefront field into PL 120. In a preferred embodiment $t_{SL}$ is, for example, at least 1 μm. Mirror 116 may be embodied, for example, by a metallic mirror, a dielectric multi-layer stack, or by any other suitable material. in some embodiments, optical device 200A includes encapsulation layer 110 sealing light source 105 of optical device 200A to seal mirror 116, SL 115 and PL 120 against oxygen and/or moisture.

Figure 2B:
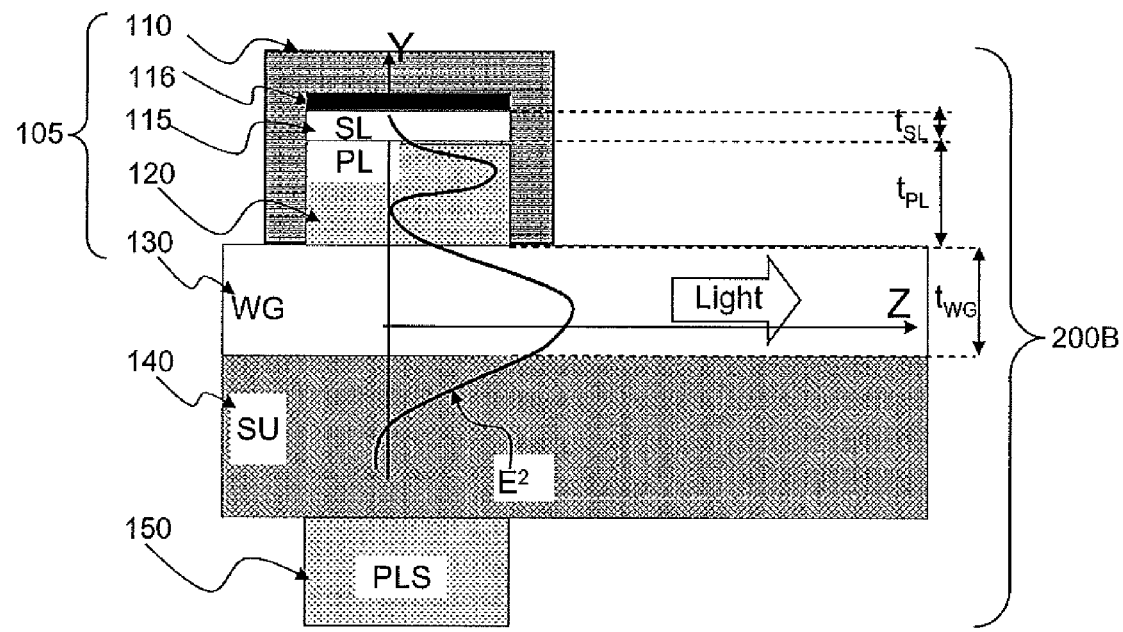
FIG. 2B is a schematic block diagram illustration of a side view of an optical device adapted to couple light emitted from a luminescent source into a low-order mode waveguide with high coupling efficiency based on a close mirror approach, according to another embodiment of the invention.

Reference is now made to FIG. 2B. To increase the light-coupling efficiency between PL 120 and WG 130, light source 105 of an optical device 200B includes mirror 116 that is placed or provided at a specific distance $t_{SL}$ in close proximity to PL 120. Mirror 116 in conjunction with WG 130 builds an effective optical cavity of a length $t_{SL}+t_{PL}$ such to potentially increase the pump-light intensity up to a factor 4. Mirror 116 is separated from PL 120 by SL 115 having thickness $t_{SL}$. In a preferred embodiment $t_{SL}$ is less than 1000 nm, particularly preferred below 300 nm, especially preferred less than 100 nm. In optical device 200B, $t_{SL}$ is chosen in such a way that the effective cavity length, the sum of $t_{SL}$ and $t_{PL}$ is half the peak wavelength of PLS 150 or a multiple thereof. Again, in some embodiments light source 105 of optical device 200B is encapsulated by encapsulation layer 110 sealing PL 120, and optionally mirror 116 and/or SL 115 against oxygen and/or moisture. It should be noted that in this approach mirror 116 can be designed in such a way that either TE or TM polarization is absorbed, thus enabling the selective coupling of one polarization into WG 130. Selective coupling increases the signal-to-noise-ratio of the coupled light, compared to signal-to-noise ratio that would otherwise be obtained without selective coupling.

Figure 3A:
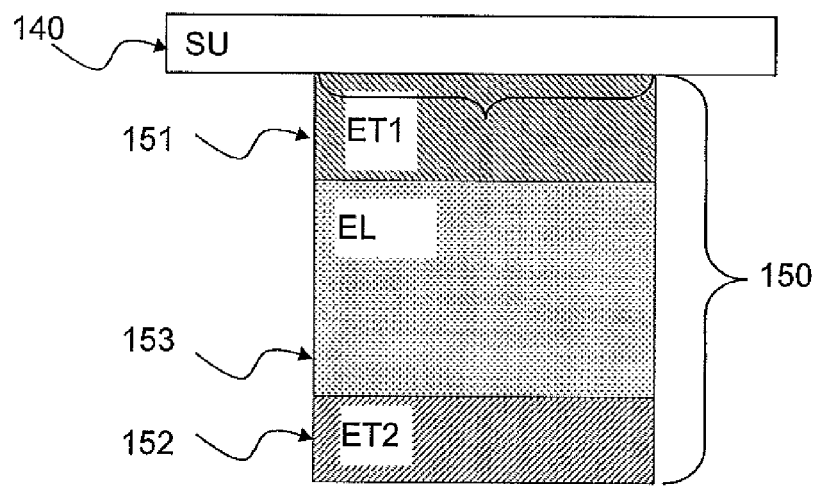
FIG. 3A is a detailed schematic block diagram illustration of a side view of an embodiment of the pump light source, according to an embodiment of the invention.

Further reference is now made to FIG. 3A. It should be noted that PLS 150 as schematically illustrated in FIG. 3A may not realizable, since in a real-world PLS the electroluminescent layer must cover the edges of the electrodes in order to avoid electrical short circuits between them. However, to simplify the discussion that follows, schematic illustration of PLS 150 is used for outlining its functional features.

As already indicated herein, PLS 150 may be implemented by means of electroluminescence (light emitting capacitor). The embodiment thereof is schematically indicated and comprises at least a first electrode layer 151, a second electrode layer 152 and at least one electroluminescent layer 153 sandwiched between electrode layer 151 and 152. In addition, PLS 150 may also include at least one dielectric layer (not shown), situated and covering at least some of the interface between electrode layer 151 and electroluminescent layer 153, or the interface between electrode layer 152 and electroluminescent layer 153. For exemplary purposes only, electrode layer 151 is hereinafter referred as to the electrode that is positioned closer to a substrate (e.g., SU) than electrode layer 152. In the said embodiment, the electrode that is closer to e.g., SU must be at least partially transparent for the light produced by electroluminescent layer 153. This may be achieved by using a suitable material that is substantially transparent or semitransparent for the said light. Such materials may be, for example, conducting oxides, semi-transparent thin metal films, conducting polymer layers as electrodes and the like.

The following is an example of how electroluminescence may be generated. For example, by applying an alternating voltage to electrode layer 151 and 152, electroluminescent layer 153 is subjected to high alternating electrical fields (e.g., $10^6$ V/cm), which in turn causes the excitation of, e.g., phosphors in electroluminescent layer 153. The dielectric layer (not shown) should minimize or at least reduce the electrical current through PLS 150.

PLS 150 may be implemented by an OLED. Again, the upper electrode layer 151, i.e. the one in contact with substrate 140, must be at least partially transparent for the light produced by the OLED. This may be achieved by using transparent conducting oxides, semi-transparent thin metal films, or conducting polymer layers as electrodes. Additional charge transport layers can be inserted between the electroluminescent layer(s) and the cathode and between the electroluminescent layer(s) and the anode. Suitable thicknesses for all these layers are in the range of, for example, 1 nm to 1 μm. Preferred are thicknesses in the range of, for example, 5 nm to 200 nm.

In the event that PLS 150 is embodied by an OLED, suitable materials for electrode layer 151 of the OLED may include, for example, substantially transparent conducting oxides, semi-transparent thin metal films, or conducting polymer layers as electrodes.

It should be noted that in the embodiments in which PLS 150 is implemented by an OLED, charge transport layers (not shown) may be sandwiched or inserted between electroluminescent layer 153 and electrode layer 151, as well as between electroluminescent layer 153 and electrode layer 152. In embodiments of the invention, the thickness for the charge transport layers may range, for example, from 1 nm to 1 μm. In preferred embodiments of the invention, the thickness of the charge transport layers may range, for example, from 5 nm to 200 nm.

Figure 3B:
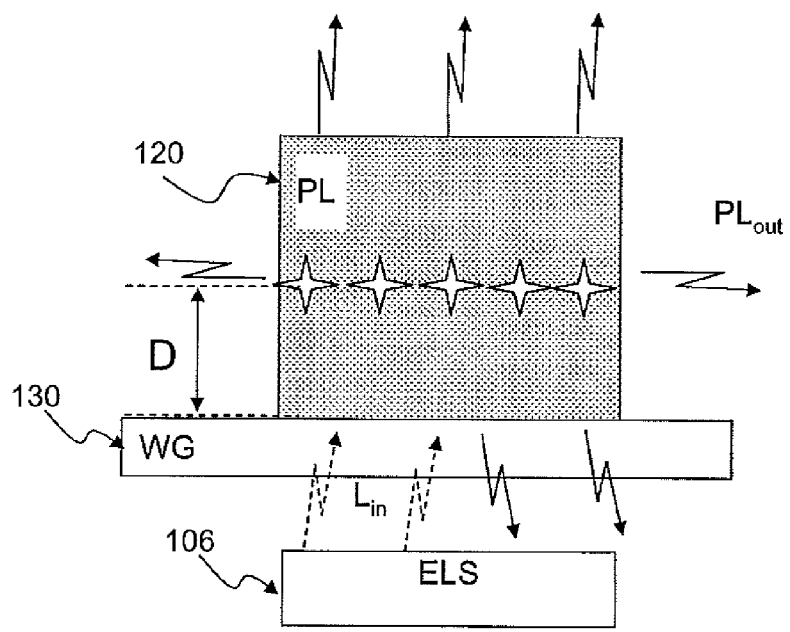
FIG. 3B is a detailed schematic block diagram illustration of a side view of a photoluminescent layer and the individual light sources thereof and an external light source operatively associated with another embodiment of the luminescent source.

Additional reference is now made to FIG. 3B. It shows a detailed view of a light source 105, according to an embodiment of the invention, wherein light source 105 includes at least one PL 120 that emits light when being irradiated with photons. Correspondingly, if PL 120 is suitably subjected to light $L_{in}$ emitted from an external light source (ELS) 106, PL 120 may absorb some of the light $L_{in}$ and emit as a result thereof light $PL_{out}$.

In embodiments, ELS 106 may be a monolithically integrated light source according to and embodied by PLS 150, or be any suitable external light source such as, for example, an ultraviolet lamp, an inorganic LED, a laser diode, a laser or an OLED on a separate substrate. At least some of the wavelength(s) of light $L_{in}$ differ from $PL_{out}$. In some embodiments of the invention, some of the photoluminescent material(s) of PL 120 schematically illustrated in FIG. 3B may be identical (and thus also substantially identical) to the electroluminescent material(s) of electroluminescent layer 153.

The thickness of PL 120 may be about equal or be smaller than, e.g., 100 μm. In some preferred embodiments of the invention, the thickness of PL 120 may be about equal or be smaller than, e.g., 10 μm. In some more preferred embodiments of the invention, the thickness of PL 120 may be about equal or be smaller than, for example, 1 μm.

The distance D between the light emitting zone(s) of PL 120 from WG 130 is an additional parameter that may have an influence on the coupling efficiency of light from PL 120 into WG 130.

For exemplary purposes only, the light emitting zones are herein schematically indicated as an assembly of point sources, which may be embodied, for example, by dipoles and/or quadrupoles and/or by any other electrical pole arrangement. In any event, sources may be arranged substantially in one plane, as is schematically indicated in FIG. 3B. Alternatively, sources may be arranged in various planes and/or may be positioned in light source 105 in a substantially random manner (not shown).

It should be noted that the rate at which sources can emit light into a given mode of WG 130 is proportional to the square of the electric field distribution $E^2$ of that given mode at the location of source. The square of the electric field distribution for the mode of order zero is schematically illustrated for example, in FIG. 1A and FIG. 1B by means of curve $E^2$. Outside WG 130 itself the electric field distribution E decays exponentially with an increase of the distance from WG 130. It may therefore be advantageous that the distance D between sources and WG 130 is about equal or smaller than the decay length of the exponential tails of the modes supported by WG 130 to ensure that light emitted from PL 120 is coupled into low-order mode WG 130. Suitable distances D between WG 130 and sources of light source 105 may be about equal to or be smaller than, for example, 5 μm. In some preferred embodiments of the invention, distance D may be about equal or be smaller than, for example, 500 nm. In some more preferred embodiments of the invention, D may be about equal or be smaller than, for example, 150 nm.

In general, the efficiency of transfer of optical power from PL 120 into a waveguide such as, for example, WG 130, may be referred to, for example, in accordance to the term "coupling efficiency" and may be expressed as the ratio between the optical power in all the modes of WG 130 and the total optical power emitted by the light source(s).

The above-mentioned requirements of efficient transfer of optical power from PL 120 into WG 130 imply, inter alia, that PL 120 ought to be as close as possible to a waveguide (e.g., WG 130) and/or that a waveguide (e.g., WG 130) should be near cutoff wavelength. Near cutoff, the waveguide modes are largely outside WG 130 and will overlap with PL 120 even when the waveguide is relatively distant from PL 120.

Light propagating in PL 120 may be subjected to other and/or additional obstacles that may cause modal loss during the propagation of light.

Figure 4A:
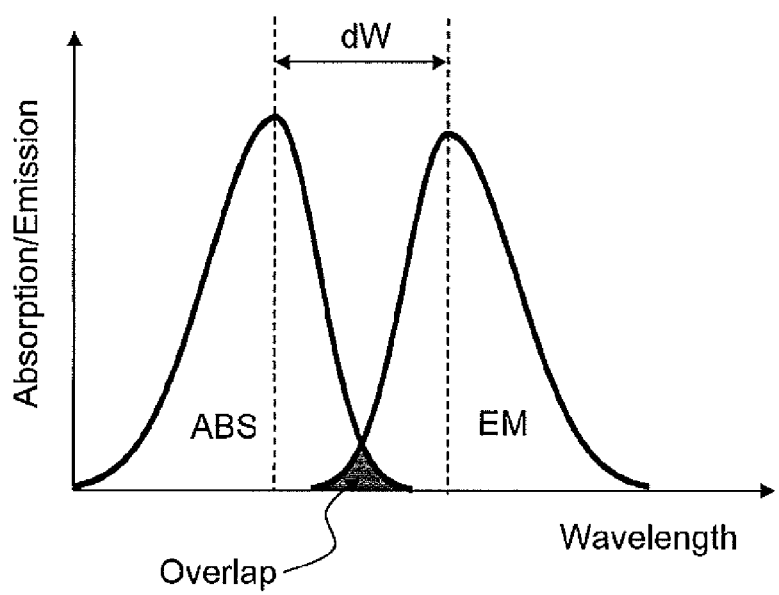
FIG. 4A shows a graph that schematically depicts an embodiment of a photo-luminescent material where the absorption peak and the photo-luminescent emission peak are well separated from each other by a large wavelength shift.

Reference is now made to FIG. 4A. In the proposed evanescent coupling scheme photons emitted from PL 120 in FIG. 1A couple into the waveguide mode depicted by the mode profile. By the inverse mechanism, light propagating inside WG 130 could couple into PL 120 and being reabsorbed. In order to avoid or reduce re-absorption it is of high importance that the absorption band and the photoluminescence emission band are spectrally well separated from each other by a wavelength shift dW. This shift dW is defined as the distance of the absorption and emission peak maxima of PL 120. Preferred dW is larger than, e.g., 50 nm, especially preferred larger than, e.g., 80 nm and particularly preferred larger than, e.g., 100 nm. In other word, the overlap between the absorption curve and the emission curve should preferably be as small as possible. In practice good candidates for PL 120 are materials with narrow absorption and emission peaks and large Stokes shifts.

Figure 4B:
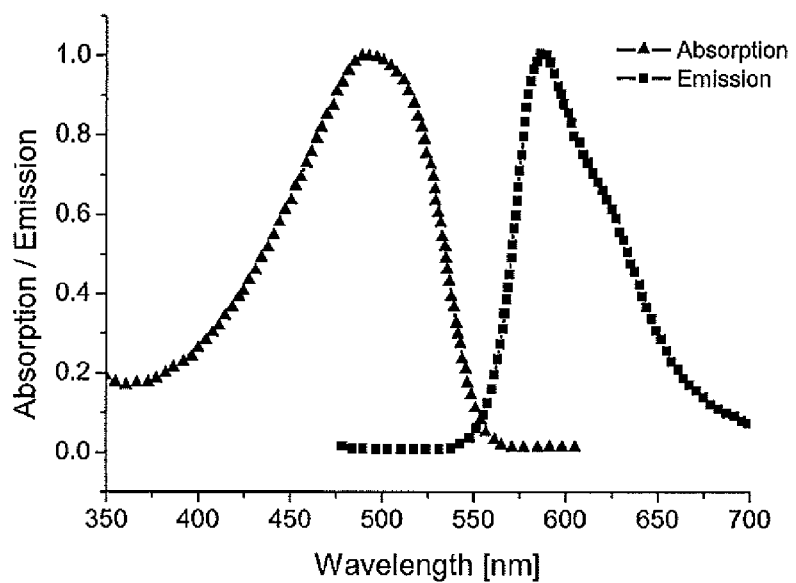
FIG. 4B shows a graph that schematically depicts absorption and emission spectra of photo-luminescent layer MEH-PPV.

Reference is now made to FIG. 4B wherein the re-emission spectrum of F8BT is schematically depicted, the re-emission spectrum being well separated from its absorption spectrum by a large Stokes shift.

Figure 5A:
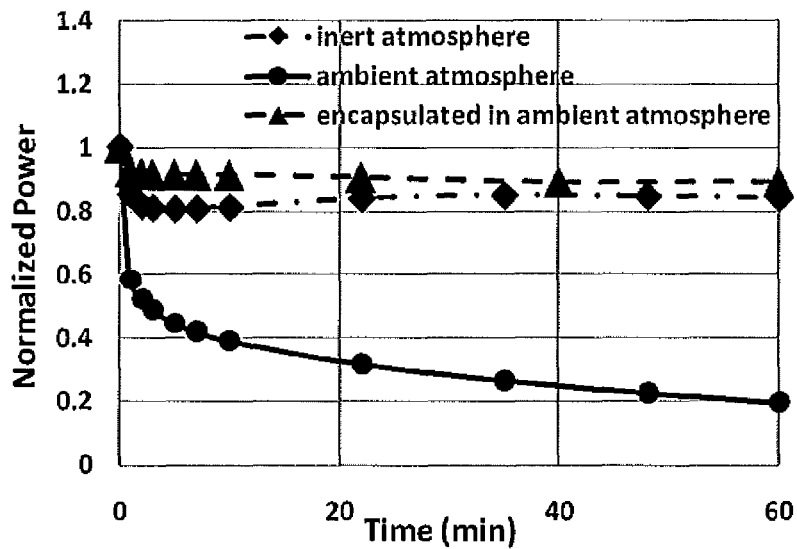
FIG. 5A shows a graph that schematically depicts normalized photo-luminescent emission power of MEH-PPV in different environmental atmospheres.

Reference is now made to FIG. 5A. It shows the importance of encapsulation of PL 120 in order to increase the lifetime. A 200 nm thick PL 120 of MEH-PPV was encapsulated by a glass slide maintained with epoxy glue. The material of encapsulated PL 120 showed stable lifetime in ambient atmosphere with variation of 10% during 1 hour.

Figure 5B:
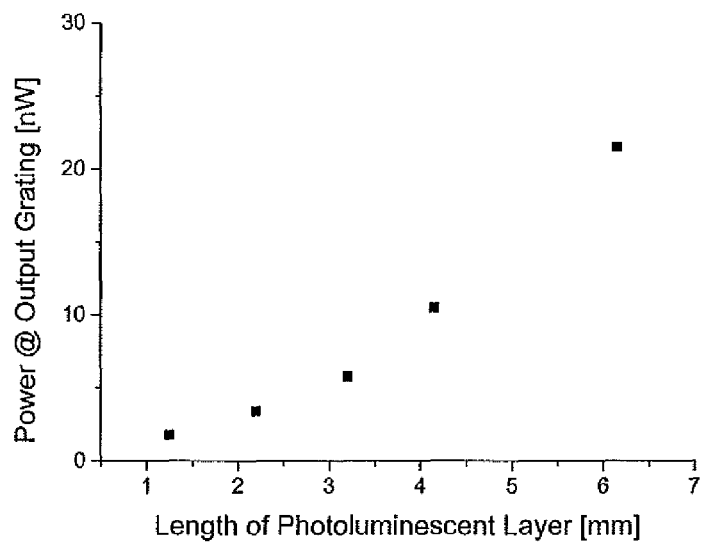
FIG. 5B shows a graph that schematically depicts the dependence of the power coupled into the waveguide as a function of the pumped length of the photoluminescent layer.

FIG. 5A shows a graph that schematically depicts normalized photo-luminescent emission power of MEH-PPV in different environmental atmospheres. Further reference is made to FIG. 5B schematically depicting the power at the output grating which is roughly proportional to the power coupled into WG 130, while it is assumed that the area of PLS 150 is much larger than the area of PL 120 and as such PL 120 is illuminated homogeneously while border effects can be neglected. In such configuration the power coupled into WG 130 scales linearly with the length of PL 120.

For the measurement depicted in FIG. 5B, the optical device had at least approximately the following parameters:
Su—material: Glass, n=1.45
WG—material: $Ta_2O_5$, n=2.2, thickness $t_{WG}$=200 nm
PL—material: American Dye Source ADS133YE, thickness $t_{PL}$=100 nm
PL 120 was excited with a large area emitter consisting of a blue inorganic LED emitting at 465 nm providing a pump intensity of 4.75 mW/cm² and a diffuser plate (not shown).

Figure 6A:
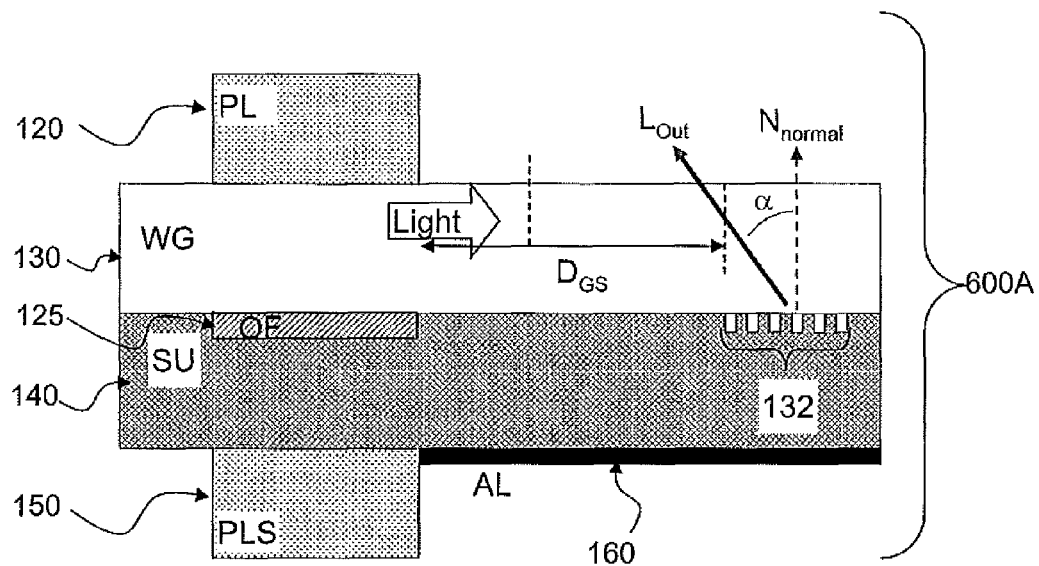
FIG. 6A is a schematic block diagram illustration of a side view of an optical device adapted to couple light emitted from the luminescent source into a low-order mode waveguide and couple it out to the air at the output grating, according to a further alternative embodiment of the invention.

Additional reference is now made to FIG. 6A and FIG. 6A. Optical devices 400A and 400B according to embodiments of the disclosed invention, may each comprise an out-coupling grating structure (GS) 132 manufactured in WG 130 adapted to couple light out of WG 130. The first grate of GS 132 (viewed from the direction of the propagation of light in WG 130) may be located at a distance $D_{GS}$ from the outermost edge of the PL 120.

Angle "α" schematically illustrates an out-coupling angle of the light ($L_{out}$) emitting from WG 130, whereby angle "α" is measured with respect to a normal "$N_{normal}$" of WG 130. The said angle "α" may be given by the following equation:

$$n_c \sin\alpha = N - \frac{\lambda}{\Lambda},$$

wherein "$n_c$" represents the refractive index of the layer cladding of WG 130 at its output. Correspondingly, "$n_c$" may represent the refractive index of air or of SU 140, depending whether GS 132 is situated on the upper or lower side of WG 130. "N" represents the effective refractive index of the waveguide mode in WG 130, "λ" the wavelength(s) of the light propagating in WG 130, and "Λ" the grating period of GS 132.

Optical devices 400A and 400B may also feature in-coupling GS 131 adapted to increase the optical coupling efficiency of light into WG 130.

In-coupling GS 131 and out-coupling GS 132 may be fabricated, e.g., as known in the art. For example, GS 131 and 132 may be fabricated by dry or wet etching techniques. Further in-coupling GS 131 and out-coupling GS 132 may be fabricated by replication from molds or Ni-maters in case that WG 130 is made of polymeric substrates or UV cast materials.

Either one or both in-coupling and out-coupling GS 131 and GS 132 may be grafted—before the deposition of WG 130 into SU 140. Alternatively, either one or both in-coupling GS 131 or out-coupling GS 132 may be grafted into WG 130 after their deposition onto SU 140.

According to some embodiments of the invention, a grating period Λ of in-coupling GS 131 and/or out-coupling GS 132 may range, for example, from 100 nm to 1 μm. In some preferred embodiments of the invention, a grating period Λ of in-coupling and out-coupling GS 131 and/or GS 132 may range, for example, from 200 nm to 500 nm. According to some embodiments of the invention, the depth of in-coupling and out-coupling GS 131 and/or GS 132, respectively may range, for example, from 1 nm to 500 nm. In some preferred embodiments of the invention, the depth of in-coupling GS 131 and/or out-coupling GS 132 and may range, for example, from 5 nm to 50 nm.

Figure 6B:
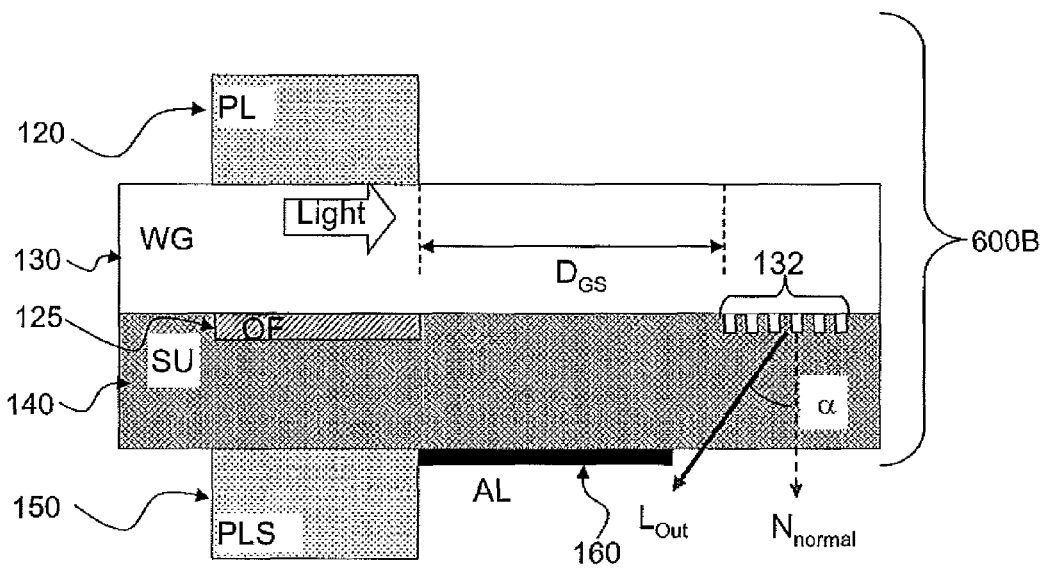
FIG. 6B is a schematic block diagram illustration of a side view of an optical device adapted to couple light emitted from the luminescent source into a low-order mode waveguide and couple it out to the substrate at the output grating, according to a yet further alternative embodiment of the invention.

The spectrally resolved output at out-coupling GS 132 can be either detected on the waveguide side (FIG. 6A) or on the substrate side (FIG. 6B). The out-coupling GS 132 could be a blazed grating, which may be most effective either towards top or bottom emission.

In embodiments of the invention, optical devices 600A and 600B include an absorbing layer (AL) 160 situated on the backside of substrate 140, like PLS 150. AL 160 is adapted to suppress substrate modes that might be excited by PLS 150. Substrate modes are undesirable since they might get coupled into a detection system (not shown), add optical noise and therefore lower the signal-to-noise ratio of optical device 600A and/or 600B.

Optical device 600A and/or 600B may be implemented as outlined hereinafter. SU 140 may be, for example, a 14 mm×57 mm glass substrate onto which a substantially planar single mode WG 130, being 150 nm thick and comprising $Ta_2O_5$, was sputter-deposited. At least approximately, parallel to the long sides of SU 140, at 2.25 mm from the substrates SU 140 edge, a substantially uniform rectangular out-coupling GS 132 of, e.g., 312 nm period and 12 nm depth may be grafted into SU 140 by employing a photolithographic process and dry etching prior the deposition of $Ta_2O_5$. In a next step PL 120 may be deposited on top of WG 130 by means of spin-coating or drop-casting. PLS 150 is mechanically coupled with SU 140 either by lamination or by being monolithically integrated with SU 140. In some embodiments, PLS 150 is embodied by an OLED. First electrode layer 151 may for example comprise of an Indium Tin Oxides (ITO) layer that was sputtered onto one side of SU 140 and subsequently patterned by chemical- or plasma etching or laser ablation or by any other method, e.g., known in the art. The subsequent charge injection layers and electroluminescent layers as well as second electrode layer 152 may be depositable by employing a procedure selected of the following group: liquid processing, vacuum deposition and lamination. In a different embodiment the OLED is processed on a separate substrate which is then laminated to the chip.

AL 160 may be embodied, for example, by a black light-absorbing film that is laminated onto the lower side of SU 140 or by a substantially black ink layer that is deposited on the lower side of SU 140 by liquid coating techniques, e.g., known in the art.

In embodiments of the invention, either one or both optical devices 600A or 600B may include OF 125 adapted to modify at least some of the light prior and/or while being coupled into WG 130 as outlined herein with reference to FIG. 1B.

Figure 7A:
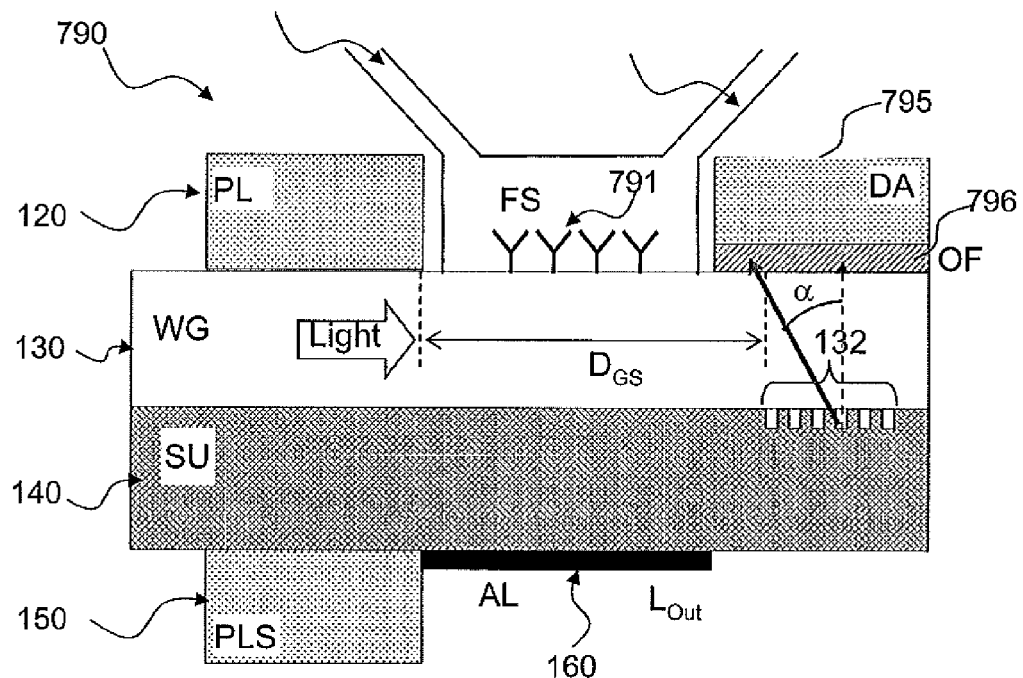
FIG. 7A is a schematic block diagram illustration of a side view of an optical device adapted to work as an optical sensor with the detector array placed or provided above the waveguide, according to an embodiment of the invention.

Reference is now made to FIG. 7A. An optical device 700A according to an embodiment of the invention may be integrated with a fluid (e.g., liquid or gas) flow cell 790 including a functionalized surface 791 for sensing applications. Sensing applications include but are not limited to chemical sensing of gas and liquids, DNA, Gen-Antigen, protein interaction, chemical interaction. Functionalized surface (FS) 791 may be located on top of WG 130 between PL 120 and out-coupling GS 132 inside flow cell 790. The optical modes in WG 130 are response to changes to FS 791 induced by a respective specimen (not shown).

In an embodiment of the invention, PL 120 lies outside flow cell 790 in order to avoid cross-contamination of specimen with the material of PL 120 and also to avoid light scattering from PL 120 into the liquid specimen. In the embodiment of optical device 700A the detection takes place on the upper side of WG 130.

In an alternative embodiment, PL 120 constitutes a sensing layer. Examples include oxygen and glucose sensors based on phosphorescent lifetime quenching of oxygen sensitive dyes such as PtOEP (2,3,7,8,12,13,17,18-Octaethyl-21H,23H-porphine platinum (II)) or PdOEP (2,3,7,8,12,13,17,18-Octaethyl-21H,23H-porphine palladium).

In an embodiment of the invention, FS 791 may be provided on top of out-coupling GS 132 or be monolithically integrated with GS 132.

In yet another embodiment an optical (not shown) microstructure may be deposited on top of WG 130 in order to increase the interaction with FS 791.

According to one embodiment of the invention, light diffracted from the out-coupling GS 132 is collected by a detector array (DA) 795 located on the lower side of the substrate next to AL 160.

Further, DA 795 may be adapted to measure the intensity and the spectral distribution—and thus specimen-induced changes thereof—of light propagating in the waveguide. According to an embodiment of the invention DA 795 includes of a one- or two-dimensional array of photodiodes or a charge coupled device or any other kind of light sensitive device having an arbitrary number of pixels. A special case of such a DA would be a single pixel detector.

Additional optical filters 796 could be integrated or placed or provided in front of DA 795 including but not limited to band-pass and edge filters and polarizer.

In an alternative embodiment DA 795 is an array of organic photodiodes that could be integrated monolithically onto SU 140 or be on a separate substrate situated below SU 140.

In yet another embodiment, DA 795 may be monolithically integrated on top of WG 130 or be on a separate substrate positioned above WG 130. In all embodiments of the invention PLS 150 may also be modulated in order to enable phase sensitive detection as for example lock-in techniques.

Figure 7B:
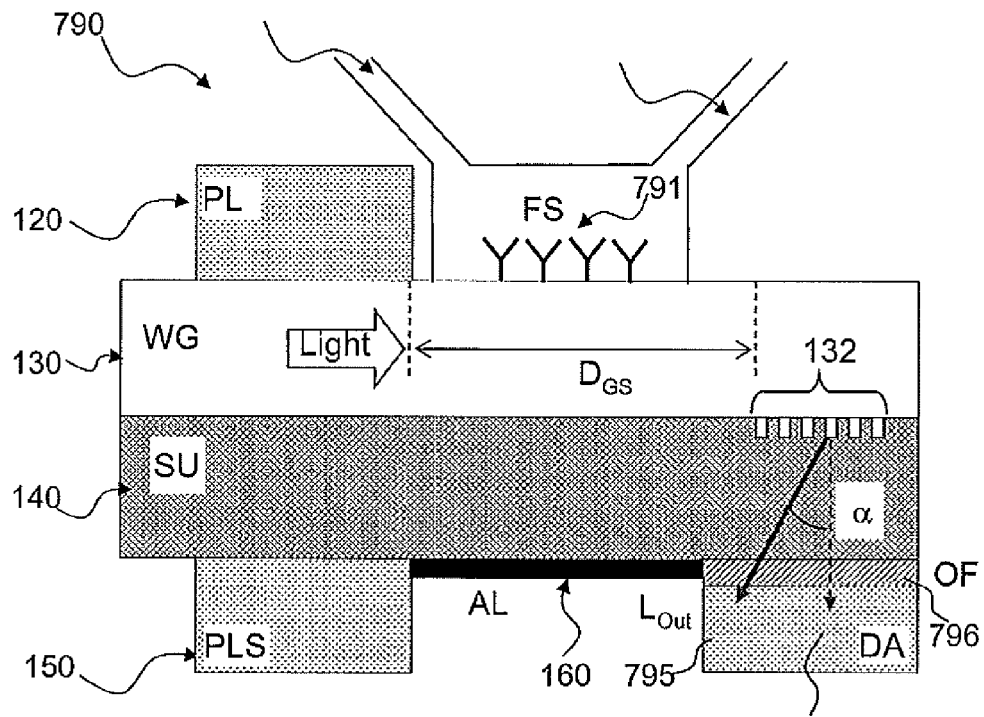
FIG. 7B is a schematic block diagram illustration of a side view of an optical device adapted to work as an optical sensor with the detector array placed below the substrate, according to an embodiment of the invention.

Reference is now made to FIG. 7B. In contrast to FIG. 7A, light in an optical device 700B is detected on the same side of SU 140 as PLS 150. This configuration has the advantage that the excitation in PLS 150 and the detection are located on one side of SU 140 790, thus facilitating encapsulation of PLS 150, which may be monolithic with SU 140 an very sensitive to water and humidity.

Figure 8A:
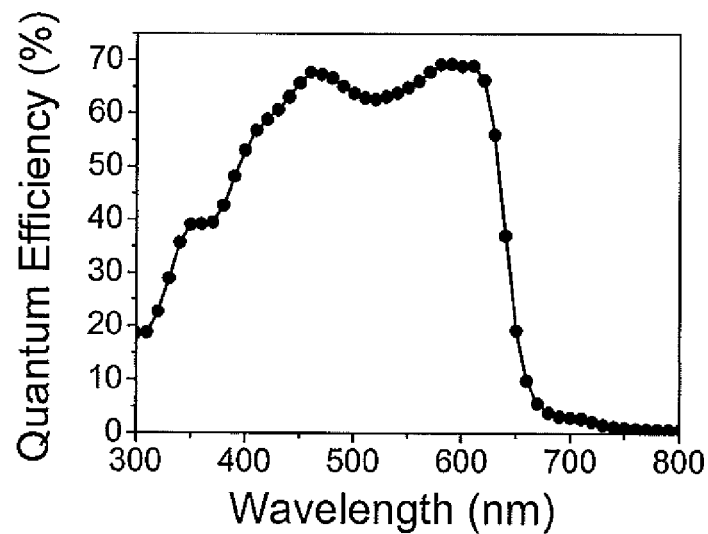
FIG. 8A shows a graph depicting the response of a P3HT: PCBM-based polymer photodiode detector (PPD) which can be used in the detector array DA in embodiments of the invention.

Additional reference is now made to FIG. 8A. In one embodiment, DA 795 includes an array of polymer photodiodes (PPDs) to detect the spectrum of the out-coupled light. The PPD-blend includes of Poly(3-hexylthiophene):phenyl-C61-butyric acid methyl ester, P3HT:PCBM with weight ratio of 1:1. The layer thickness of the PPD is 240 nm and has been optimized for optimal external quantum efficiency, on/off ratio and lifetime. As a result, we report on organic photodiodes with EQE of 70% at 0V bias, an on/off current ratio of 106 at −1V and 40 mW/cm2 illumination, dark current densities below 10 nA/cm2 at −1V, and a lifetime of at least 3000 hours. More details can be found in M. Ramuz et al, Organic Electronics 9 (2008), page 369-376. PPDs based on a blend of Poly(3-hexylthiophene):phenyl-C61-butyric acid methyl ester (P3HT:PCBM, 1:1 by weight) are at least sensitive in the 400-640 nm range.

Figure 8B:
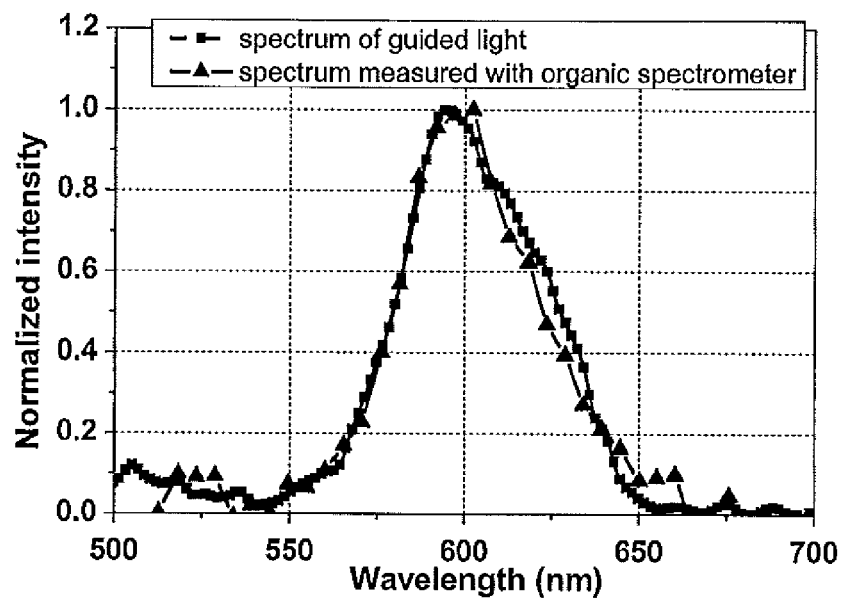
FIG. 8B shows a graph depicting the spectra of the guided light measured by the organic spectrometer or detector array DA of FIG. 8A (triangles) and by an inorganic spectrometer (squares) set up in similar measuring condition—influence of the grating out-coupling angle condition are similar for both measurements.

Reference is now made to FIG. 8B, schematically depicting the spectrum measured with an integrated organic spectrometer based on an array of PPDs. Experimental spectral resolution was obtained by comparing the c bandwidth (80 nm) of the guided spectrum with the spectra obtained with the PPDs array. By taking into account that the PPDs have a sensitivity cut-off at 640 nm, one can estimate the full width at half maximum (FHWM) of the guided light at 60 nm. Pixel to pixel spectral resolution of $\Delta \approx 5$ nm FWHM was achieved with this set-up when the PL material is pumped by an inorganic LED. By using an OLED, a spectral resolution of $\Delta \approx 7$ nm was achieved. Signal to noise ratio is about 10.

Figure 9:
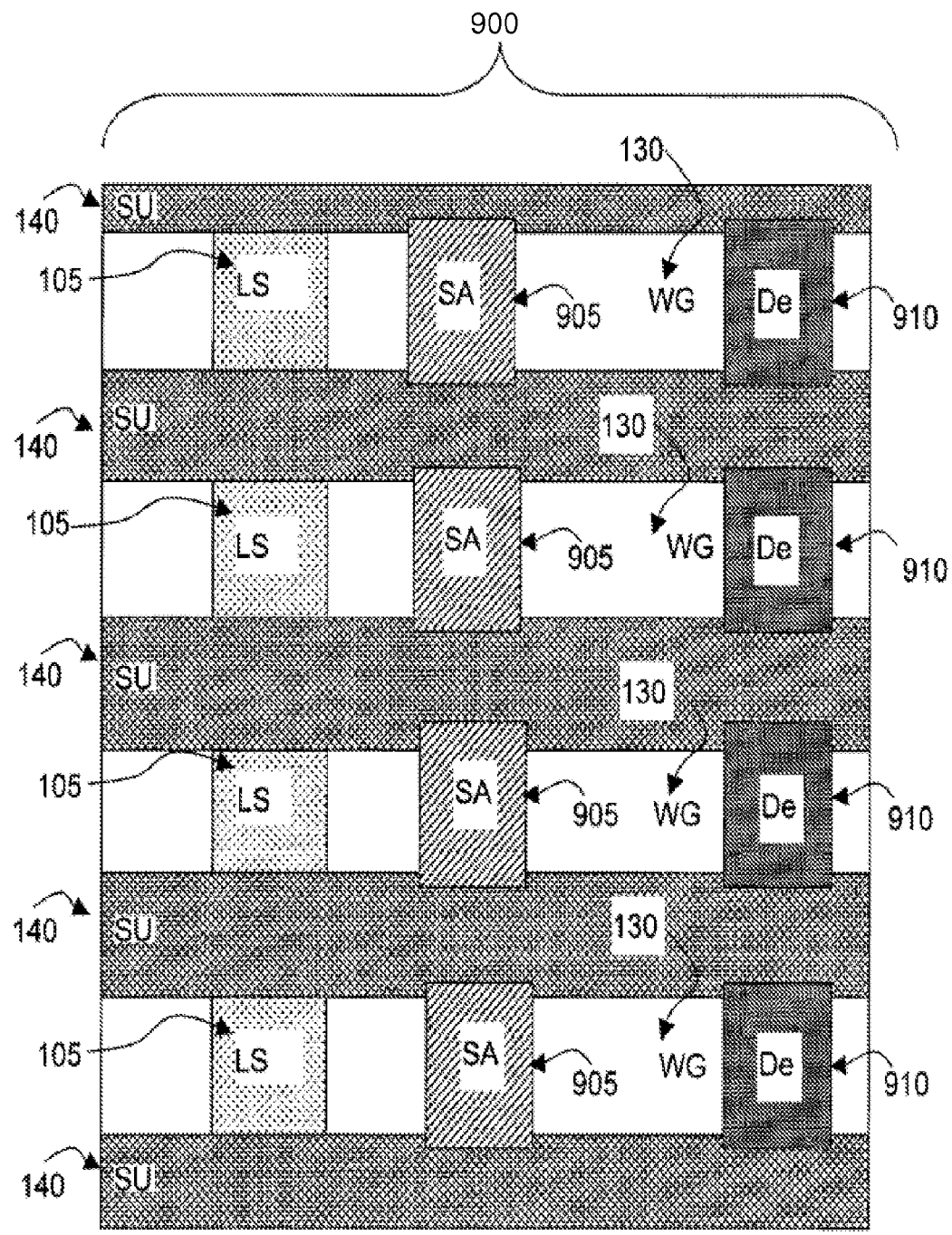
FIG. 9 is a schematic block diagram illustration of a top view of an integrated optical system, according to an embodiment of the invention.

Reference is now made to FIG. 9. An optical device according to each of the embodiments of the invention may be integrated into an optical system 900, which may may include at least one photoluminescent layer (e.g., PL 120), which may be coupled to a structure comprising of at least one SU 140 and at least one low-order mode waveguide 130, which may be a thin film of high-index layer deposited on SU 140. Optical system 900 may further include at least one sensing area (SA) 905 and at least one detector (DE) 910, whereby the at least one SA 905 and DE 910 are substantially aligned with respect to PL 120.

At SA 905, light may interact in WG 130 with a respective specimen (not shown). Further, DE 910 may be adapted to measure the intensity and the spectral distribution—and thus specimen-induced changes thereof—of light propagating in the respective WG 130.

Optical system 900 comprising one or more optical devices according to embodiments of the invention offer many advantages over systems known in the art, which rely on one or more external light sources, such as laser diodes for example.

First, the integrated solution provided by optical system 900 allows substantial savings in space requirements since a) no bulky external light sources are needed and b) the proposed luminescent PLS 150 are extremely thin and may have in some embodiments of the invention a thickness of only a few micrometers. In some embodiments of the invention, PLS 150 may for example have a thickness of less than 1 µm.

Second, alignment of elements in optical system 900 can be performed with relatively fault-prone free and time saving procedures.

Third, optical system 900 facilitates the integration of a plurality of light sources by depositing PL 120 having different operational specifications. For example, a first and a second PL 120 may emit light having respectively different wavelengths $\lambda_1$ and $\lambda_2$. Therefore, a highly parallel integrated optical system, such as optical system 900, comprising of an array of monolithically integrated light sources can be realized.

An alternative embodiment of the invention may rely on an external PLS 150 embodied, for example by an UV LED. A single PLS 150 may pump different types of PLS 150 and thus generate a wide range of different wavelength.

In some embodiments of the invention, a plurality of PLS 150 and PL 120 may be fabricated by additive print technologies such as for example, ink-jet or gravure printing, which is state-of-the-art in the field of OLEDs (cf. B.-J. de Gans et al., Inkjet Printing of Polymers: State of the Art and Future Developments, Advanced Materials 16, p. 203, 2004, hereinafter referred to as "Gans et al.").

The fabrication methods described, inter alia, by Gans et al., allow the deposition of a variety of PLS 150/PL 120 pairs on a substrate in accordance to respective predefined locations. In addition, the fabrication methods enable juxtaposing neighboring PL 120 at a distance of a few µm from each other. For example, a lateral resolution of a few µm of a matrix of a plurality of identical or various light sources is achievable.

Fourth, each of the PLS 150/PL 120 pairs described herein are compatible with flexible substrates, thus enabling fully integrated optical systems on a polymer basis.

Fifth, due to a combination of the above reasons, optical system 900 offers the potential to be fabricated in a cost-effective way. The reasons therefore are, for example: Polymeric substrates may be used instead of glass substrates, (high-volume) print processes may be used instead of standard processes such as vacuum deposition methods and photolithographic patterning. PLS' 150 do not have to be integrated in a cost-intensive packaging step to fabricate optical system. In case an external PLS 150 is used only the at least one PL 120 needs to be aligned properly.

Due to the advantages described herein, optical system 900 may be used in association with a wide range of applications, including medical diagnostics (e.g. DNA screening), automotive (e.g. rain sensor), industrial (e.g. gas sensor), security and information technologies. A prototypical application is a low-cost, disposable, card-type, multiple-channel fully integrated optical biosensor for point-of-care diagnostics.

In some embodiments of the invention, WG 130 may be made of any suitable material. For example, WG 130 may be made of a dielectric material having a relatively high index of refraction. Non-limiting examples of materials of which WG 130 may be made of include $Ta_2O_5$, $TiO_2$, $HfO_2$, $SiO_xN_y$, poly(1-naphthyl methacrylate), poly(1-naphthyl methacrylate-co-glycidyl methacrylate)glycidyl methacrylate, poly(2,4,6-tribromophenyl methacrylate), poly(2,4,6-tribromophenyl methacrylate-co-glycidyl methacrylate)glycidyl methacrylate, poly(2,6-dichlorostyrene), poly(2-chlorostyrene), poly(2-vinylthiophene), poly(bis(4-iodophenoxy) phosphazene), poly(N-vinylphthalimide), poly(pentabromobenzyl acrylate), poly(pentabromobenzyl methacrylate), poly(pentabromobenzyl methacrylate-co-glycidyl methacrylate)glycidyl methacrylate, poly(pentabromophenyl acrylate), poly(pentabromophenyl acrylate-co-glycidyl methacrylate)glycidyl methacrylate, poly(pentabromophenyl methacrylate), poly(pentabromophenyl methacrylate-co-glycidyl methacrylate)glycidyl methacrylate, poly(pentachlorophenyl methacrylate), poly(vinyl phenyl sulfide), and poly(vinyl phenyl sulfide-co-glycidyl methacrylate)glycidyl methacrylate. Additionally, losses due to SU 140 should be as low as possible.

Electrode layer 151 may be made of indium thin oxide (ITO), zinc oxide (ZnO), especially In or Al doped ZnO, tin oxide ($SnO_2$), especially Sb and F doped $SnO_2$, gold, silver, nickel, poly(3,4-ethylenedioxythiophene)poly(styrenesulfonate), polyanyline, polyacetylene and polypyrrole. Electrode layer 152 may be made of calcium, barium, lithium fluoride, aluminum and silver. EL may be made of poly[2-methoxy-5-(2-ethylhexyl-oxy)-1,4-phenylene-vinylene], poly[2,5-bis(3,7-dimethyloctyloxy)-1,4-phenylene-vinylene], poly[2-methoxy-5-(3,7-dimethyl-octyloxy)-1,4-phenylenevinylene], poly(9,9-dioctylfluorenyl-2,7-diyl), poly[9,9-di-(2-ethylhexyl)-fluorenyl-2,7-diyl], poly(9,9-di{2-[2-(2-methoxy-ethoxy)ethoxy]ethyl}fluorenyl-2,7-diyl), poly[2-(6-cyano-6-methyl-heptyloxy)-1,4-phenylene], poly(2,5-dioctyl-1,4-phenylene), poly[9,9-di-(2-ethylhexyl)-fluorenyl-2,7-diyl], poly[(9,9-dioctyl-2,7-divinylene-fluorenylene)-alt-co-{2-methoxy-5-(2-ethyl-hexyloxy)-1,4-phenylene}], poly[(9,9-dioctylfluorenyl-2,7-diyl)-co-(1,4-vinylenephenylene)], poly[9,9-dioctylfluorenyl-2,7-diyl)-co-1,4-benzo-{2,1'-3}-thiadiazole)], poly[(9,9-dihexylfluorenyl-2,7-diyl)-alt-co-(2-methoxy-5-{2-ethylhexyloxy}-1,4-phenylene)], poly[(9,9-dihexylfluorenyl-2,7-diyl)-co-(2,5-p-xylene)], poly[(9,9-di (3,3'-N,N'-trimethyl-ammonium)propylfluorenyl-2,7-diyl)- alt-(9,9-dioctylfluorenyl-2,7-diyl)]diiodide salt, poly[(9,9-dioctylfluorenyl-2,7-diyl)-co-(N,N'-diphenyl)-N,N'di(p-butyl-oxy-phenyl)-1,4-diaminobenzene)], poly[(9,9-dioctylfluorenyl-2,7-diyl)-co-(1,4-benzo-{2,1',3}-thiadiazole)], 4,4'-bis(9-ethyl-3-carbazo-vinylene)-1,1'-biphenyl, 9,10-Bis[(9-ethyl-3-carbazoyl)-vinylenyl]-anthracene, 4'4-bis(diphenylvinylenyl)-biphenyl, 1,4-bis(9-ethyl-3-carbazo-vinylene)-2-methoxy-5-(2-thylhexyloxy)-benzene, 4,4'bis(diphenylvinylenyl)-anthracene, 1,4-bis(9-ethyl-3-carbazo-vinylene)-9,9-dihexyl-fluorene, 9,9,9',9',9'',9''-hexakis(hexyl)-2,7';2',7''-trifluorene, 9,9,9',9',9'',9''-hexakis(octyl)-2,7',2',7''-trifluorene, 9,9,9',9',9'',9'',9''',9'''',9''''-decakis(hexyl)-2,7';2',7'',2''',7''';2''',7''''-pentafluorene, 9,9,9',9',9'',9'',9''',9''',9'''',9'''',9''''',9'''''-dodecakis(hexyl)-2,7';2',7'',2''',7''';2''',7''',2'''',7'''',2''''',7'''''-heptafluorene, 3,7-bis-(9,9-di-n-hexylfluoren-2-yl)-dibenzothiophene-S,S-dioxide, 3,7-Bis[7-(9,9-di-n-hexylfluoren-2-yl)]-9,9-di-n-hexylfluoren-2-yl]dibenzothiophene-S,S-dioxide, 2,7-Bis[7-(9,9-di-n-hexylfluoren-2-yl)dibenzothiophene-S,S-dioxide-3-yl]-9,9-di-n-hexylfluorene, lithium tetra(2-methyl-8-hydroxyquinolinato)boron, lithium tetra(8-hydroxy-quinolinato)boron, bis(8-hydroxyquinolinato)zinc, bis(2-methyl-8-hydroxy-quinolinato)zinc, tris(benzoylacetonato) mono-(phenanathroline)europium, tris(dibenzoylmethane) mono-(phenanthroline)europium(III), tris (dibenzoylmethane)-mono(5-aminophenanthroline) europium (III), Tris(dinaphtoylmethane)-mono (phenanthroline)europium (III), tris(dibiphenoylmethane)-mono(phenanthroline)europium (III), tris (dibenzoylmethane)-mono(4,7-diphenylphenanthroline)-europium (III), tris[di(4-(2-(2-ethoxyethoxy)ethoxy) benzoylmethane)]mono(phenanthro-line)europium (III), tris (2-phenylpyridine)iridium (III), tris(8-hydroxyquinolato)-aluminum (III), tris(8-hydroxyquinolato)gallium (III), platinum (III) [2(4,6-difluorophenyl)pyridinato-N,C2)-(acetyl-acetonate), iridium (III) bis(2-(4,6-difluorephenyl) pyridinato-N,C2), iridium (III) tris(2-(4-totyl)pyridinato-N, C2), iridium (III) bis(2-(2'-benzo-thienyl)pyridinatoN,C3') (acetyl-acetonate), tris(1-phenylisoquinoline)iridium (III), bis(1-phenylisoquinoline)-(acetylacetonate)iridium (III), tris (2-(2,4-difluorophenyl)pyridine)iridium (III), iridium(III)bis (2-methyldibenzo-[f,h]quinoxaline)(acetylacetonate), bis(2-(9,9-dibutylfluorenyl)-1-isoquinoline(acetylacetonate), bis (2-(9,9-dihexylfluorenyl)-1-pyridine)(acetylacetonate) iridium(III), Tris(3-methyl-1-phenyl-4-trimethyl-acetyl-5-pyrazoline)terbium(III), dichlorotris(1,10-phenanthroline) ruthenium(II) and rubrene.

The charge transport layers (not shown) may be made of any suitable material such as, for example, N,N'-bis(3-methylphenyl)-N,N'-bis(phenyl)benzidine, N'N'-bis(4-methylphenyl)-N,N'-bis(phenyl)benzidine, N,N'-bis(2-naphtalenyl)-N—N'-bis(phenylbenzidine), 1,3,5-tris(3-methyldiphenyl-amino)benzene, N,N'-bis(1-naphtalenyl)-N—N'-bis(phenylbenzidine), 4,4',4''-tris(N,N-phenyl-3-methylphenylamino)triphenylamine, 4,4',N,N'-diphenylcarbazole, poly[(9,9-dihexylfluorenyl-2,7-diyl)-co-(N,N'bis{p-butylphenyl}-1,4-diamino-phenylene)], poly[9,9-dioctylfluorenyl-2,7-diyl)-co-(N,N'bis(4-butylphenyl-1,1'-bipheny-lene-4,4-diamine)], poly(N,N'-bis(4-butylphenyl)-N,N'-bis(phenyl)benzidine, 2-(4-biphenylyl)-5-phenyl-1,3,4-oxadiazole, 2-(4-tert-Butylphenyl)-5-(4-biphenylyl)-1,3,4-oxadiazole, 3,5-bis(4-tert-butylphenyl)-4-phenyl-4H-1,2,4-triazole, 3-(biphenyl-4-yl)-5-(4-tert-butylphenyl)-4-phenyl-4H-1,2,4-triazole, bathocuproine, bathophenanthroline, tris(8-hydroxyquinolato)-aluminum (III), poly(3,4-ethylenedioxythiophene)poly(styrenesulfonate), polyaniline, polyacetylene and polypyrrole.

Electroluminescent layer 153 may be made of, for example, ZnS, ZnSe, SrS, and GaN doped with rare earth or transition metal ions (ZnS:Mn, SrS:Cu, GaN:Er). The insulating layer (not shown) may be made of, for example, barium titanate, $SiO_2$, $Al_2O_3$, poly(2,2,2-trifluoroethyl methacrylate), poly(2,2,3,3,3-pentafluoropropyl methacrylate), poly (1,1,1,3,3,3-hexafluoroisopropyl acrylate, poly(1,1,2,4,4,5, 5,6,7,7-decafluoro-3-oxa-1,6-heptadiene), poly(2,2,2-trifluoroethyl acrylate), poly(2,2,3,3,3-pentafluoropropyl acrylate), poly(2,2,3,3,4,4,4-heptafluorobutyl acrylate), poly (2,2,3,3,4,4,4-heptafluorobutyl methacrylate), poly(2,2,3,3-tetrafluoropropyl methacrylate), poly(2,2,3,3-tetrafluoropropyl acrylate), poly(2,2,3,4,4,4-hexafluorobutyl acrylate), poly(2,2,3,3,4,4,4-hexafluorobutyl methacrylate), poly[4,5-difluoro-2,2-bis(trifluoromethyl)-1,3-dioxole-co-tetrafluoroethylene]dioxole, poly(1,1,1,3,3,3-hexafluoroisopropyl methacrylate-co-glycidyl methacrylate)glycidyl methacrylate, poly(1,1,1,3,3,3-hexafluoroisopropyl methacrylate), poly(1,1,1,3,3,3-hexafluoroisopropyl methacrylate-co-glycidyl methacrylate)glycidyl methacrylate, poly(2,2,2-trifluoroethyl methacrylate-co-glycidyl methacrylate)glycidyl methacrylate, poly(2,2,3,3,3-pentafluoropropyl methacrylate-co-glycidyl methacrylate)glycidyl methacrylate, poly(2, 2,3,3,4,4,4-heptafluorobutyl methacrylate-co-glycidyl methacrylate glycidyl methacrylate, poly(2,2,3,3-tetrafluoropropyl methacrylate-co-glycidyl methacrylate) glycidyl methacrylate, poly(2,2,3,4,4,4,-hexafluorobutyl methacrylate-co-glycidyl methacrylate)glycidyl methacrylate, poly(2,2,3,3-tetrafluoropropyl methacrylate-co-glycidyl methacrylate)glycidyl methacrylate, poly(2,2,2-trifluoroethyl methacrylate), poly(2,2,2-trifluoroethyl methacrylate-co-glycidyl methacrylate)glycidyl methacrylate, poly(2,2,3,3,3-pentafluoropropyl methacrylate), poly(2, 2,3,3,3-pentafluoropropyl methacrylate-co-glycidyl methacrylate), poly(2,2,3,3,4,4,4-heptafluorobutyl methacrylate), poly(2,2,3,3,4,4,4-heptafluorobutyl methacrylate-co-glycidyl methacrylate glycidyl methacrylate, poly(2,2,3,3-tetrafluoropropyl methacrylate), poly(2,2,3,3-tetrafluoropropyl methacrylate-co-glycidyl methacrylate)glycidyl methacrylate, poly(2,2,3,4,4,4-hexafluorobutyl methacrylate), poly(2, 2,3,4,4,4,-hexafluorobutyl methacrylate-co-glycidyl methacrylate)glycidyl methacrylate, poly(pentafluorostyrene), poly(pentafluorostyrene-co-glycidyl methacrylate)glycidyl methacrylate, poly(tert-butyl methacrylate-co-glycidyl methacrylate)glycidyl methacrylate, poly(methyl methacrylate), polycarbonate, cyclo olefin copolymers (COCs), or sol-gel materials.

Suitable substrates for the organic devices are glass, polymer, especially polymeric foil, paper or metal. Flexible substrates are well suited for roll-to-roll processes. The substrate can be for example a flexible polymer foil like acrylonitrile butadiene styrene ABS, polycarbonate PC, polyethylene PE, polyetherimide PEI, polyetherketone PEK, poly(ethylene naphthalate) PEN, poly(ethylene therephtalate) PET, polyimide PI, poly(methyl methacrylate) PMMA, poly-oxy-methylene POM, mono oriented polypropylene MOPP, polystyrene PS, polyvinyl chloride PVC and the like. Other materials like paper (weight per area 20-500 $g/m^2$, preferably 40-200 $g/m^2$), metal foil, (for example Al—, Au—, Cu—, Fe—, Ni—, Sn—, steel-foil etc., especially surface modified, coated with a lacquer or polymer, are suitable too. The substrate can be coated with a barrier layer or a barrier layer stack to increase the barrier properties (J. Lange and Y. Wyser, "Recent Innovations in Barrier Technologies for Plastic Packaging—a Review", Packag. Technol. and Sci. 16, 2003, p. 149-158).

E.g. inorganic materials like $SiO_2$, $Si_3N_4$, $SiO_xN_y$, $Al_2O_3$, $AlO_xN_y$ and the like are often used. They can be deposited e.g. in vacuum processes like evaporation, sputtering or chemical vapour deposition CVD, especially plasma enhanced CVD (PECVD). Other suitable materials are mixtures of organic and inorganic materials deposited in a sol-gel process. Such materials can even be deposited in a wet coating process like e.g. gravure printing. Barrier properties are obtained by multilayer coatings of organic and inorganic materials as described in WO03/094256A2. In the following the term substrate shells denote substrates with and without barrier coatings.

It will be appreciated by persons skilled in the art that the disclosed technique is not limited to what has been particularly shown and described hereinabove.

What is claimed is:

1. An optical device generating light by luminescence comprising a substrate having a front side and a backside, a waveguide, a pump light source and a photoluminescent layer,
    wherein said waveguide is evanescently coupled with said photoluminescent layer;
    wherein said pump light source is provided opposite to said photoluminescent layer at said backside of said substrate;
    wherein said waveguide is positioned between said substrate and said photoluminescent layer;
    wherein said pump light source is adapted to pump said photoluminescent layer to emit light such that at least some of said emitted light is evanescently coupled into said waveguide.

2. The optical device according to claim 1, wherein said waveguide is a low-order waveguide with a thickness in the range of 10 nm to 10 μm.

3. The optical device according to claim 1, wherein the absorption and emission peak of light emitted by said photoluminescent layer are spectrally separated by at least 50 nm.

4. The optical device according to claim 1 comprising an encapsulation layer sealing said photoluminescent layer.

5. The optical device according to claim 1, further comprising a spacer layer and a mirror, wherein said spacer layer has a thickness $t_{SL}$ and is disposed between said photoluminescent layer and said mirror, and wherein said mirror is adapted to reflect and re-inject at least some of the light pumped by said pump light source back into said photoluminescent layer.

6. The optical device according to claim 5, wherein said thickness $t_{SL}$ is at least twice as large as the penetration depth $L_P$ of a wavefront field into said photoluminescent layer.

7. The optical device according to claim 1 comprising an optical filter structure adapted to modify at least some of the light being coupled into said waveguide.

8. The optical device according to claim 7, wherein said optical filter structured is positioned between said waveguide and said photoluminescent layer.

9. The optical device according to claim 7, wherein said optical filter is positioned between said substrate and said waveguide.

10. An optical system comprising at least one substrate having a front side and a backside, a plurality of waveguides, a plurality of pump light sources and a plurality of photoluminescent layers,
    wherein said plurality of waveguides are evanescently coupled, respectively, with said plurality of photoluminescent layers,
    wherein said plurality of pump light sources are provided on said backside of said at least one substrate opposite to said plurality of photoluminescent layers, respectively;
    said plurality of waveguides are positioned between said plurality of photoluminescent layers and said at least one substrate; and
    wherein said plurality of pump light sources are adapted to pump said plurality of photoluminescent layers to emit light such that at least some of said emitted light is optically coupled into said plurality of waveguides, respectively.

11. The optical device according to claim 7, wherein the thickness $t_{SL}$ has a magnitude of at least 1 μm.

12. The optical device according to claim 1, wherein said waveguide comprises an out-coupling grating structure for coupling light out from said waveguide.

13. The optical device according to claim 1, further comprising a light sensitive device located on said waveguide and operative to detect light coupled out from said waveguide.

14. An optical device generating light by luminescence comprising a substrate having a front side and a backside, a waveguide, a pump light source and a photoluminescent layer, wherein said waveguide is evanescently coupled with said photoluminescent layer;
    wherein said pump light source is provided opposite to said photoluminescent layer at said backside of said substrate;
    wherein said photoluminescent layer is positioned between said substrate and said waveguide; and
    wherein said pump light source is adapted to pump said photoluminescent layer to emit light such that at least some of said emitted light is evanescently coupled into said waveguide.

15. The optical device according to claim 14, further comprising a spacer layer and a mirror, wherein said spacer layer has a thickness $t_{SL}$ and is disposed between said photoluminescent layer and said mirror, and wherein said mirror is adapted to reflect and re-inject at least some of the light pumped by said pump light source back into said photoluminescent layer.

16. The optical device according to claim 14, wherein said waveguide comprises an out-coupling grating structure for coupling light out from said waveguide.

17. The optical device according to claim 16, further comprising a light sensitive device located on said waveguide and operative to detect light coupled out from said waveguide.

18. The optical system of claim 14 further comprising a plurality of sensing areas and a plurality of detectors, whereby the plurality of sensing areas and detectors are substantially aligned with respect to the plurality of photoluminescent layers.

19. An optical system comprising at least one substrate having a front side and a backside, a plurality of waveguides, a plurality of pump light sources, and a plurality of photoluminescent layers, wherein said plurality of waveguides are evanescently coupled, respectively, with said plurality of photoluminescent layers,
    wherein said plurality of photoluminescent layers are positioned between said substrate and said plurality of waveguides;
    wherein said plurality of pump light sources are provided on said backside of said at least one substrate opposite to said plurality of photoluminescent layers, respectively, and
    wherein said plurality of pump light sources is adapted to pump said plurality of photoluminescent layers to emit light such that at least some of the emitted light is optically coupled into said plurality of waveguides, respectively.

20. The optical system of claim 19 further comprising a plurality of sensing areas and a plurality of detectors, whereby the plurality of sensing areas and detectors are substantially aligned with respect to the plurality of photoluminescent layers.

* * * * *